(12) United States Patent
Jones et al.

(10) Patent No.: US 11,899,692 B2
(45) Date of Patent: Feb. 13, 2024

(54) DATABASE REDUCTION BASED ON GEOGRAPHICALLY CLUSTERED DATA TO PROVIDE RECORD SELECTION FOR CLINICAL TRIALS

(71) Applicant: Laboratory Corporation of America Holdings, Burlington, NC (US)

(72) Inventors: Stephen Michael Jones, Rickmansworth (GB); Michelle Lsl Jones, Rickmansworth (GB); Michael Brian Garcia, West Windsor, NJ (US); Elizabeth Martina Marshallsay, Las Vegas, NV (US); Rachael Haig, Wilmslow (GB)

(73) Assignee: Laboratory Corporation of America Holdings, Burlington, NC (US)

( * ) Notice: Subject to any disclaimer, the term of this patent is extended or adjusted under 35 U.S.C. 154(b) by 56 days.

(21) Appl. No.: 17/602,440

(22) PCT Filed: Apr. 7, 2020

(86) PCT No.: PCT/US2020/027025
§ 371 (c)(1),
(2) Date: Oct. 8, 2021

(87) PCT Pub. No.: WO2020/210206
PCT Pub. Date: Oct. 15, 2020

(65) Prior Publication Data
US 2022/0208313 A1 Jun. 30, 2022

Related U.S. Application Data (60) Provisional application No. 62/833,328, filed on Apr. 12, 2019.

(51) Int. Cl.
*G06F 16/28* (2019.01)
*G16H 10/20* (2018.01)
(Continued)

(52) U.S. Cl.
CPC .......... *G06F 16/285* (2019.01); *G06F 16/215* (2019.01); *G06F 16/24578* (2019.01); *G16H 10/20* (2018.01)

(58) Field of Classification Search
CPC . G16H 10/20; G06F 16/215; G06F 16/24578; G06F 16/285; G06Q 10/0631
See application file for complete search history.

(56) References Cited

U.S. PATENT DOCUMENTS

| 11,281,801 B2* | 3/2022 | Tong ...................... G16H 50/70 |
| 2007/0067278 A1 | 3/2007 | Borodziewicz et al. |

(Continued)

FOREIGN PATENT DOCUMENTS

| CA | 3056387 A1 | 9/2018 |
| GB | 2475430 A | 5/2011 |
| WO | 2003021485 A2 | 3/2003 |

OTHER PUBLICATIONS

International Search Report and Written Opinion, dated Aug. 10, 2020, 11 pages.
CA3, 134,488 , "Office Action", dated Oct. 20, 2023, 5 pages.

*Primary Examiner* — Pierre M Vital
*Assistant Examiner* — Cecile H Vo
(74) *Attorney, Agent, or Firm* — Kilpatrick Townsend & Stockton LLP (57) ABSTRACT

Aspects and features relate to computationally reducing the size or complexity of a database in order to improve the speed and efficiency with which such a database is processed by a computing system in order to identify investigators for clinical trials. In some aspects, a processing device performs operations including identifying data sources for geographically clustered data containing corresponding descriptors for database records. The operations further include formatting the corresponding descriptors to produce standardized, corresponding descriptors, and matching each standardized, (Continued)

corresponding descriptor to produce a record score for the descriptor. The record scores can be combined to produce an overall score for each database record and the database record can be selected and written to the data store based on the overall score.

20 Claims, 5 Drawing Sheets

(51) Int. Cl.
   *G06F 16/215*    (2019.01)
   *G06F 16/2457*   (2019.01)
   *G06F 16/24*     (2019.01)

(56) References Cited

U.S. PATENT DOCUMENTS

| | | | |
|---|---|---|---|
| 2010/0005048 A1 | 1/2010 | Bodapati et al. | |
| 2010/0088245 A1 | 4/2010 | Harrison et al. | |
| 2010/0332258 A1* | 12/2010 | Dahlke | G06Q 99/00 |
| | | | 705/2 |
| 2013/0304504 A1 | 11/2013 | Powell | |
| 2013/0342542 A1* | 12/2013 | Brant | G16H 10/20 |
| | | | 345/440.2 |
| 2015/0339570 A1* | 11/2015 | Scheffler | G06N 3/04 |
| | | | 706/27 |
| 2016/0125171 A1* | 5/2016 | Finken | G06F 16/285 |
| | | | 705/2 |
| 2016/0300040 A1 | 10/2016 | Dietlin et al. | |
| 2019/0355445 A1* | 11/2019 | Jones | G16H 10/60 |
| 2020/0043612 A1* | 2/2020 | McNair | G16H 50/20 |

* cited by examiner

DATABASE REDUCTION BASED ON GEOGRAPHICALLY CLUSTERED DATA TO PROVIDE RECORD SELECTION FOR CLINICAL TRIALS

CROSS-REFERENCE TO RELATED APPLICATION

This application is a U.S. national phase of International Application PCT/US2020/027025 filed Apr. 7, 2020, which claims priority to and filing benefit of U.S. Provisional Application No. 62/833,328 filed Apr. 12, 2019, each of which is incorporated herein by reference in its entirety.

TECHNICAL FIELD

This disclosure generally relates to data processing techniques to eliminate duplicate, inconsistent, or otherwise misleading records in a database. More specifically, but not by way of limitation, this disclosure pertains to reducing the size or complexity of a database using such techniques in order to improve the speed and efficiency with which such a database is processed by a computing system in order to identify investigators for clinical trials based on geographic and clinical performance considerations.

BACKGROUND

Clinical trials are an important part of the process of the introduction of new treatments into a healthcare system. Such new treatments may include novel vaccines, compositions (e.g. pharmaceutical compositions), dietary supplements, medical and/or dietary choices, and/or medical devices. Clinical trials may be utilized to generate data on safety, efficacy, patient compliance, ease of use and other topics relating to the treatment. Clinical trials may vary in size and cost, and they can involve a single research center or multiple research centers in a single country or in multiple countries.

Over the course of time, physicians practicing medicine choose to be trained so that they can participate in trials as clinical trial investigators. Investigators may change the location of work, get married etc., resulting in seemingly different investigator entries in a database of clinical investigators. A clinical trial investigator database increases in size and complexity as investigator details are added. Combining information from several sources accrued over time through merger and acquisition, perpetuates the situation, creating a database that contains multiple instances of the same individual over time. Database queries may return an overestimate of the number of investigators used previously and the depth of experience with a specific investigator may be diluted across multiple entries. Manual review of database entries is time-consuming and prone to error, especially if the task is divided across more than one individual.

SUMMARY

In one example, a system includes a data store, a non-transitory computer-readable medium including computer program code, and a processing device communicatively coupled to the data store and the non-transitory computer-readable medium. The processing device is configured for executing the computer program code to perform operations. The operations include identifying data sources for geographically clustered data containing corresponding descriptors for database records to be written to the data store. The operations further include formatting the corresponding descriptors to produce standardized, corresponding descriptors, and matching each standardized, corresponding descriptor to produce a record score for the descriptor. The operations further include combining the record scores for the standardized, corresponding descriptors to produce an overall score for each database record and selectively writing each database record to the data store based on the overall score to compile a database.

In another example, a method includes identifying data sources for geographically clustered data containing corresponding descriptors for database records to be written to a data store. The method further includes formatting the corresponding descriptors to produce standardized, corresponding descriptors, and matching each standardized, corresponding descriptor to produce a record score for the descriptor. The method further includes combining the record scores for the standardized, corresponding descriptors to produce an overall score for each database record and selectively writing each database record to the data store based on the overall score to compile a database.

In another example, a non-transitory computer-readable medium includes computer program code executable by a processor to cause the processor to perform operations. The operations include identifying data sources for geographically clustered data containing corresponding descriptors for database records to be written to the data store. The operations further include formatting the corresponding descriptors to produce standardized, corresponding descriptors, and matching each standardized, corresponding descriptor to produce a record score for the descriptor. The operations further include combining the record scores for the standardized, corresponding descriptors to produce an overall score for each database record and selectively writing each database record to the data store based on the overall score to compile a database.

In some examples, each database record corresponds to a clinical trial investigator, a clinical trial site corresponding to a clinical trial investigator, or both, and the operations further include producing the geographically clustered data using spatial cluster analysis to determine a number of prospective clinical trial subjects within a specified distance of a prospective clinical trial investigator.

DETAILED DESCRIPTION

Aspects and features of this disclosure provide a system that uses computer algorithms to determine the similarity of database entries to reduce the manual effort of a quality control check, adjudication of borderline cases, or both. These algorithms can be run automatically as new data are added, thus maintaining the database quality and keeping the database size as small as possible. These optimizations ensure faster and more resource-efficient processing of data when computerized selection of clinical trial investigators is employed.

In some examples, a system identifies sources for data containing corresponding descriptors for database records to be written to a data store. The data store includes a database for use in selecting investigators for clinical trials. The data store can include other databases, including a database for use in selecting subjects for the clinical trials. In some examples, the system also formats the corresponding descriptors for consistency and matches standardized, corresponding descriptors to produce a record score. The record scores can be combined to produce an overall score for each database record, and a database record can be written or not (selectively written), based on the score in order to compile a reduced-size database of clinical trial investigators.

The matching described above can be performed in some aspects using a Damerau-Levenshtein method to produce a Damerau-Levenshtein score. The Damerau-Levenshtein score can then be used to provide a binary score that determines whether the database record is used in the database of clinical trial investigators. A machine-learning model trained using known matches and mismatches can be used to improve the efficiency and accuracy of the matching. Adaptive feasibility can be used to fine-tune clinical trial investigator selection. Additionally, once a clinical trial is in process, the data stores described above can be updated based on clinical trial information.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure.

Figure 1:
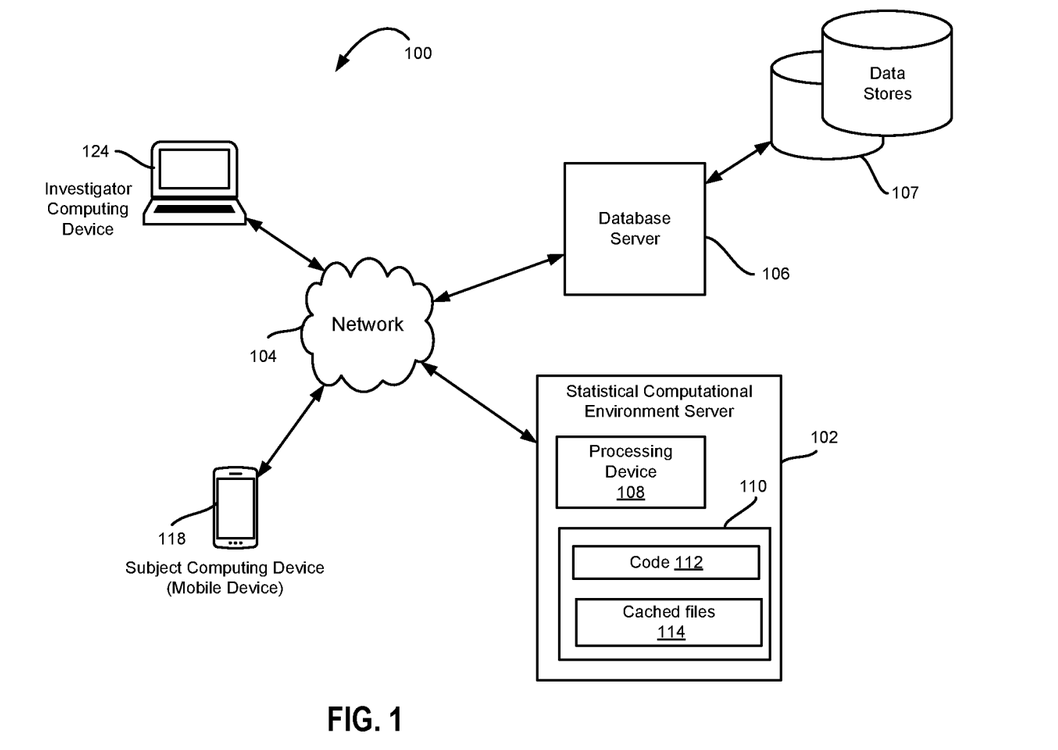
FIG. 1 is a block diagram depicting a system for providing database record selection for clinical trials according to aspects of the present disclosure.

Referring now to the drawings, FIG. 1 depicts an example of a system 100 for providing clinical trial investigator and subject selection according to some aspects. FIG. 1 depicts examples of hardware components of a system 100. The system 100 includes a statistical computational environment server (computational server) 102. Computational server 102 may be a computer or other machine that provides cluster analysis, modeling, and calculations needed for database reduction. The computational server 102 may include one or more other systems. For example, the computational server 102 may include adapters, routers, etc., for accessing communications networks. In this example, computational server 102 is connected to data network 104. The data network 104 can also be incorporated entirely within (or can include) the Internet, an intranet, an extranet, or a combination thereof. In one example, communications between two or more systems or devices can be achieved by a secure communications protocol, such as secure sockets layer ("SSL") or transport layer security ("TLS"). The system 100 includes a database server 106 connected to computational server 102 through network 104. Database server 106 is connected to data stores 107, which can include various databases, for example, databases corresponding to, or including information about, clinical trial investigators, clinical trial subjects, or other clinical trial information.

Still referring to FIG. 1, computational server 102 further includes processing device 108 communicatively coupled to a non-transitory memory device 110. Non-transitory memory device 110 includes a computer-readable medium that is used to store computer program code 112 for causing processing device 108 to perform operations for database reduction, database record selection and supporting functions according to aspects of the present disclosure. Non-transitory memory device 110 may also include cached files 114, such as database records currently being used by the processing device to perform these operations. Processing device 108 can include a processor or multiple processors, and non-limiting examples of a processing device include a field-programmable gate array ("FPGA"), an application-specific integrated circuit ("ASIC"), a microprocessor, etc.

Continuing with FIG. 1, data network 104 in system 100 connects computational server 102 to client computing devices 118 and 124. Computing device 118 is a mobile device by which a clinical trial subject can access information about a clinical trial via, for example, an app or the Web. Computing device 124 is a computer system that a clinical trial investigator or personnel associated with a clinical trial investigator can use to access information about clinical trials. The numbers of devices depicted in FIG. 1 are provided for illustrative purposes. Different numbers of devices may be used. For example, while each device, server, and system in FIG. 1 is shown as a single device, multiple devices may instead be used. Data networks 104 may include one or more of a variety of different types of networks, including a wireless network, a wired network, or a combination of a wired and wireless network.

Memory device 110 is at least in part capable of storing computer program code or instructions executable by the processing device and retaining such stored information when powered off. A non-transitory computer-readable medium including in memory device 110 can include electronic, optical, magnetic, or other storage devices capable of providing the processing device with computer-readable instructions or other program code. Such a medium may store the instructions on an installation server prior to installation in or on the servers pictured in FIG. 1. Non-limiting examples of a computer-readable medium include (but are not limited to) magnetic disk(s), memory chip(s), read-only memory (ROM), random-access memory ("RAM"), an ASIC, a configured processing device, optical storage, or any other medium from which a computer processing device can read instructions.

Figure 2:
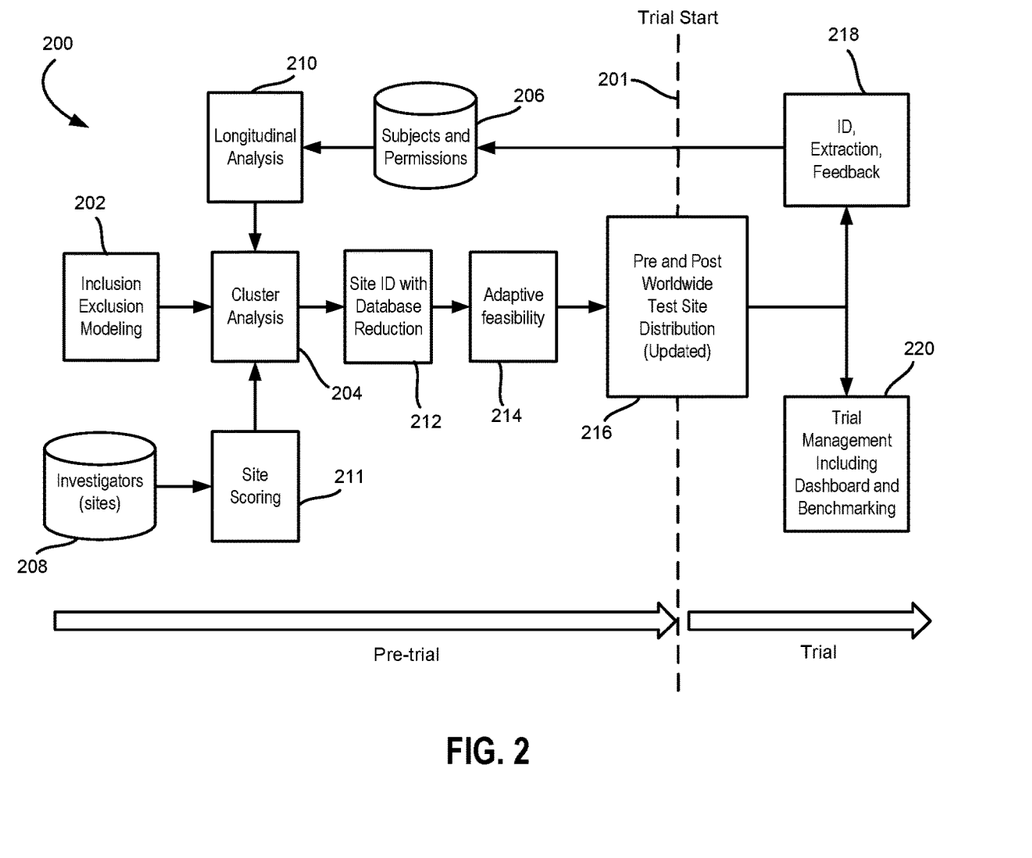
FIG. 2 is a software entity flow diagram depicting a system for providing database record selection for clinical trials according to aspects of the present disclosure.

FIG. 2 is software entity flow diagram depicting a software system 200 for providing database record selection and other functions for clinical trials according to aspects of the present disclosure. The software entities generally on the left side of FIG. 2 are used pretrial, as indicated by the arrows near the bottom. After clinical trial start 201, the software entities at the right side of FIG. 2 manage the clinical trial. Software block 202 provides study protocol design services, including modeling to determine inclusion and exclusion criteria. In order to study a patient population of the appropriate disease state and level of diversity, investigators define criteria that determine whether or not a patient is eligible for a trial. Inclusion and exclusion criteria can encompass patient characteristics (e.g., age, genetic profile) as well as disease and treatment-specific characteristics including prior laboratory test results relating to the disease and/or condition. An additional parameter is the number of subjects needed for the clinical trial. The clinical trial parameters may further include desired timing for enrolling subjects and/or investigator sites as well as a proposed timeline for completing the clinical trial.

Block 204 of system 200 provides cluster analysis to identify geographic clusters of subjects around clinical investigators based on specified distances, and to identify additional investigators for clusters of subjects that are too far away from a known or engaged investigator. The cluster analysis makes use of a database 206 of prospective clinical trial subjects, which includes information on the subjects' permissions granted for clinical studies, past results, and clinical information. The cluster analysis also makes use of database 208 of clinical trial investigators and clinical trial sites. These databases can reside in data stores 107. Longitudinal analysis 210 is applied to the data from database 206 to provide historical perspective on the data. Longitudinal analysis includes data on the last used specimens from subjects, as well as data on analyte levels over time for prospective test subjects.

Site scoring block 211 provides rankings of test sites based on the quality of investigators as determined based on to historical performance. Throughout this disclosure, the term "investigator" can be used interchangeably with the term "site" when discussing clinical trials. A site may be a particular lab or research organization that corresponds to an investigator, or with which a specified investigator is affiliated.

For spatial clustering, each possible subject comprises $I_{cn(k)}$ wherein c=1 and n=1 identifies the first investigator location within the first country with k possible subjects within the defined distance (k dependent on c and n); c=1 and n=2 identifies the second possible investigator location within the first country and so on for C countries and N=1, . . . N(c) investigator locations with k(nc) possible subjects. A spatial or "geographic" cluster as determined by cluster analysis block 204 may be represented by a minimization of the number of countries C and $\Sigma n_c$, such that:

$$\text{Probability} \left( \sum_{c=1}^{C} \sum_{n=1}^{N(c)} k_{nc} = \text{Total Required Subjects} \right) > p$$

where p is set at a level commensurate with the level of acceptable certainty of meeting study timelines and actual conversion of subjects into clinical trial patients. Location information may comprise latitude and longitude, GPS data, a zip code, a physical address and/or a postal code may be used as to determine latitude and longitude. Clinical trial parameters are used to query the databases to determine possible subjects and investigators for a clinical trial. The databases provide information relating to each possible subject including, but not limited to, the subject's geographic location. Similarly, the databases provide investigator information relating to each possible investigator including, but not limited to, an investigator's geographic location. In some examples, where insufficient numbers of experienced, clinical investigators exist, the cluster analysis 204 can provide a list of potential investigators that could be used if trained. For example, if a trial subject is also a physician, but with no experience as a clinical investigator, training the physician to be an investigator for a current clinical trial can be considered.

Continuing with FIG. 2, software block 212 identifies test sites (investigators) from clustered data. In order to make this process as computationally efficient as possible, software block 212 also includes a database reduction technique according to aspects described herein. This database reduction technique is described in detail below with respect to the remaining figures. Site identification block 212 determines worldwide distribution and country-site mix for a clinical trial using a country-site distribution engine. Site identification can include collecting bids for clinical trials based on historical recruitment rates as well as based on regulatory time requirements for each country in a country site distribution, Software block 212 can also provide a graphical tool that lists investigators and sites previously used, their ranking based on historical performance, and their geographic distribution. Data regarding observed country-level screening rates can also be displayed.

During the pretrial stages for a typical clinical investigation, potential investigators and subjects are contacted in responses are collected. Initial contacts result in responses that may change the selected distribution of subjects, test sites, clinical investigators, or other parameters, Adapted feasibility software block 214 updates all of this information as final responses alter the optimal geographic clustering and distribution of subjects and investigators.

Worldwide test site distribution software block 216 provides pre-award and post-award modeling. This modeling software tool provides test site distribution based on country specific recruitment rates and requirements. It provides time frames for a clinical trial and requirements based on those time frames. Block 216 also includes a country-site mix calculator. Country-site mix and other determinations can be updated during the trial. Software block 216 manages a clinical investigation both before and after the investigation has commenced. Test site distribution software makes database record selections to ingest data in order to do calculations. These calculations are made faster and more efficient than otherwise possible by ensuring that the data in the databases is clean, that is, consistently formatted with no duplications caused by such issues as changes in spelling of names or changes in biographic information over time. This process can be referred to herein as data reduction, data deduplication, or database reduction.

Still referring to FIG. 2, software block 218 provides site identification, subject identification, extraction of test information and data about both, and feedback into database 206 so that the database is kept up to date for future clinical trials. Trial management software block 220 provides benchmarking, communications, and appropriate dashboards for interaction with both subjects and investigators. Information from these dashboards can be displayed and input can be received, as examples, through client computing devices 118 and 124.

The software entities in system 200 ingests real-world clinical data (including laboratory diagnostic test results) and enable a user to assess the impact of inclusion/exclusion criteria of a protocol on the available pool of people with the disease, with the potential of designing a more efficient trial. Clustering uses the proximity of patients to the best suited trial investigators to identify investigators with a larger density of available patients nearby. It also supports planning for the required number of countries and investigators for the trial. User interfaces provide the ability to run complex mathematical and statistical procedures without technical knowledge within a controlled environment that prevents misapplication.

The system utilizes robust statistical and mathematical algorithms running in the statistical computational environment server 102. Linear programming techniques are applied to determine potential country-site distributions that achieve the trial timelines based on up-to-date regulatory submission timelines in each country and screening rates from similar trials performed previously. In some examples, the statistical computational environment may be established using a statistical programming language such as R in order to provide for the filtering, arranging, grouping, summarizing, and visualizing of data.

Figure 3:
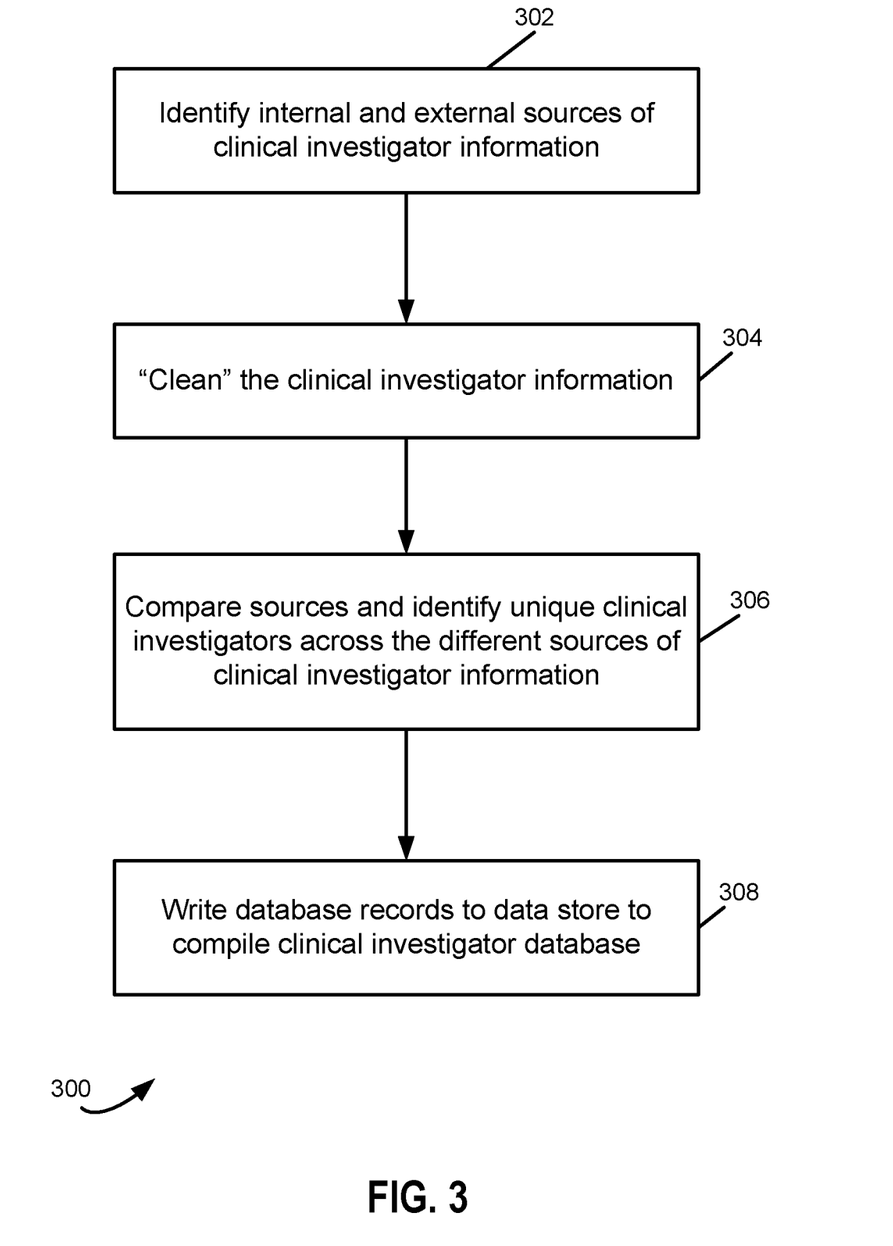
FIG. 3 is a flowchart illustrating a process of database reduction used in a system for database record selection according to aspects of the present disclosure.

FIG. 3 is a flowchart illustrating a process 300 for database reduction according to aspects of the present disclosure. Process 300 provides for compiling a list of unique clinical trial investigators from sources of un-standardized (no cleaning of spellings and no attempt to make entries consistent in format either between or within a data source) information. Common components of pieces of information contained within each source are identified and compared between sources, generating a similarity score for each component. The similarity scores for each component are then combined to give an overall similarity score for the clinical trial investigator entry for each pairwise comparison of investigators both within a source and between sources. Identification of a value (classifier) for the score that defines a binomial outcome ("Match", "No Match") allows for the process to function efficiently.

At block 302 of process 300, internal and external sources of clinical investigator information are identified. At block 304, the clinical investigator information is cleaned to make entries consistent in format. At block 306, database records from different sources are compared and unique clinical investigators across the different sources of clinical investigator information are identified. At block 308, database records are written to a data store to compile the clinical investigator database that is used in determining the worldwide test site distribution and in orchestrating the clinical trial. The reduction of the size of the database can be referred to herein as deduplication or reduction, as duplicate database entries are automatically identified and eliminated, which reduces the size of the database.

Figure 4:
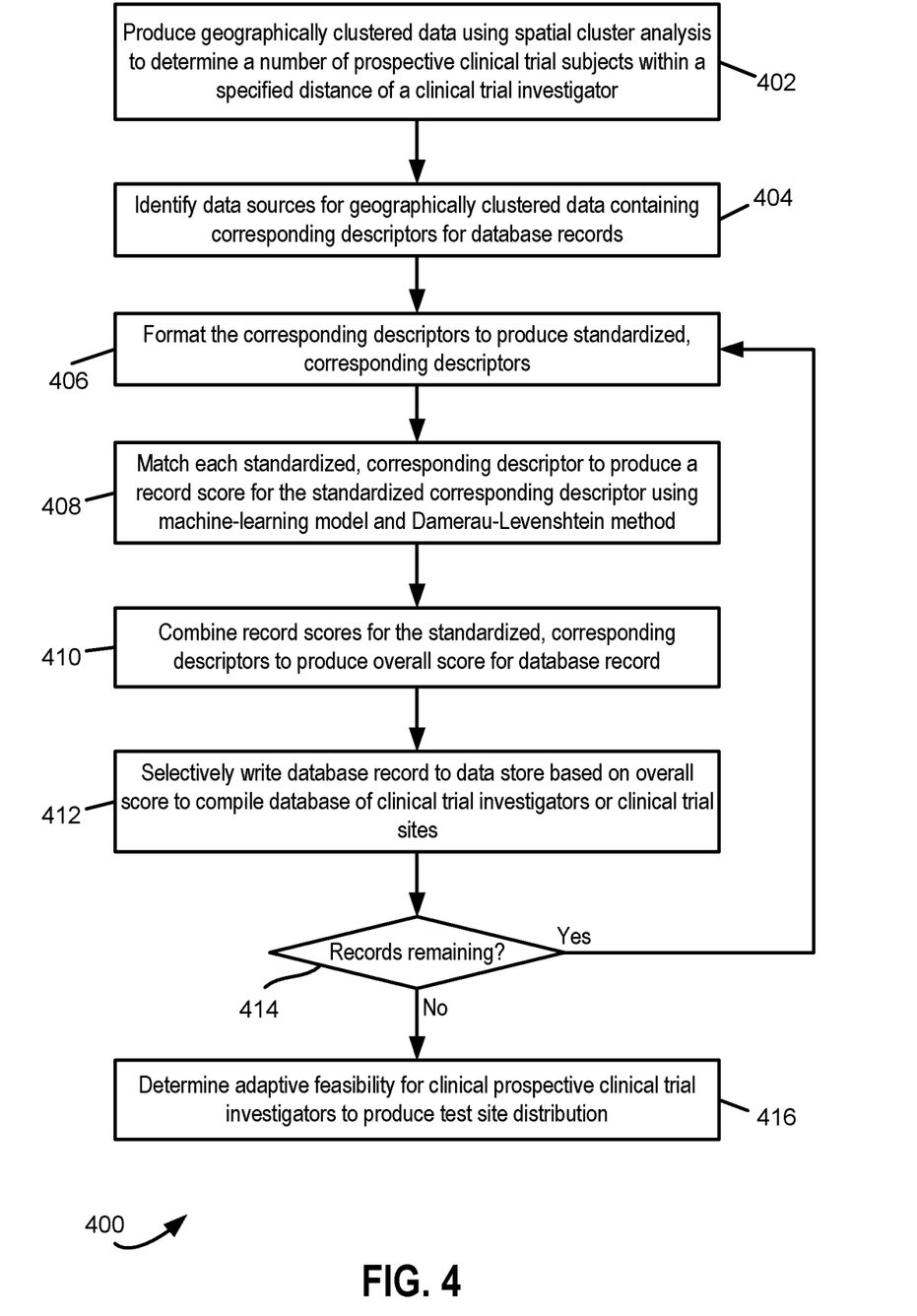
FIG. 4 is a flowchart illustrating a process of compiling and using a database of clinical investigators for clinical trials according to aspects of the present disclosure.

FIG. 4 is a flowchart illustrating an example of a process 400 of compiling and using a database of clinical investigators for clinical trials according to aspects of the present disclosure. At block 402, the geographically clustered data is produced by processing device 108 using cluster analysis 204. The geographically clustered data uses the cluster analysis to determine a number of prospective clinical trial subjects within a specified distance of a prospective clinical trial investigator. At block 404, sources for the geographically clustered data containing corresponding descriptors for database records are identified. Data sources are identified that contain similar descriptors of the entries being databased; the number of descriptors selected needs to be the minimum necessary, while the set of descriptors needs to be a sufficient subset of all potential descriptors so that they collectively, uniquely identify an entry if complete information is present.

In some examples, an external source can be assumed to be the most accurate source in terms of unique entries. This source is external to the enterprise designing the clinical trial, as otherwise, the database reduction process would be unnecessary. For purposes of this example, one can assume there are three internal sources of data that need to be combined and deduplicated, and one external source of data that is assumed to be a deduplicated database.

At block 406 of FIG. 4, processing device 108 formats the corresponding descriptors to produce standardized, corresponding descriptors. For purposes of this example, one can assume there are five descriptors of interest for each database entry in each of the sources selected: investigator name, investigator site street address, investigator city, investigator postal code, and investigator email address. In this example, the investigator name includes a forename and surname combined. For Southeast Asian names, the matching can be applied twice, once reversing the order of the names in one database entry to accommodate the cultural norm of persons being referenced by your family name first. The investigator site street address in this example includes a mandatory building/block number for definitive identification of location, since there are locales where a street alone would be insufficient. For example, Harley Street in London, UK is world-famous as a street of private-practice physicians; using just Harley Street in a database entry would not differentiate two investigators of the same name who both work there. Each descriptor needs to be standardized in format as much as possible to facilitate the matching process. Standardizations that can be incorporated in the process, as examples, include the conversion of all alphabetic characters to lower case and the removal of punctuation marks.

Still referring to FIG. 4, at block 408, each standardized corresponding descriptor is matched to produce a record score for the standardized corresponding descriptor. In some examples, a machine-learning model is used. In some examples, the Damerau-Levenshtein (DL) method is used for text matching. Each descriptor undergoes the text-matching process separately, both within the data source entries and between data sources. As an example, consider four forenames: Stephen, Steve, Steven, Stephanie. The DL algorithm determines the number of insertions, deletions and character transpositions that are required to get from one name to the other. For example, the difference between Steve and Steven produces a DL score of 1 as the change only requires the addition of the letter "n." The DL score based on the difference between Stephanie and Stephen is 3 (addition of "i" and "e" and change of "a" to "e"). The difference between Stephanie and Steve produces a DL score of 5 (removal of "h," "a," "n," and "i," and replacing "p" with "v").

The length of the text being matched can be important. For example, the difference between "dog" and "cat" produces a DL score of 3, which is the highest for a 3-letter word. For this reason, the DL score is modified by dividing the DL score by the number of characters in the longer of the two words being compared in order to produce a modified DL score. Using the example based on "Steve" and "Steven" form above, the difference is scored as 1/6 and the difference between "Stephanie" and "Steve" is scored as 5/9. The final alteration is to subtract the modified score from 1 and round to produce a binary, final, record score from the modified DL score, where a score of 1 represents a match and a score of 0 represents a total mismatch.

For the street address descriptor, a modification is needed if the street number is considered critical. As one example, the system can be designed so that the numeric parts of the descriptors being compared need to match exactly, otherwise a record score of 0 is assigned to the record in question. With any of the matching described above, a query to a user can be raised for cases where there is a good match on all descriptors other than a specific portion such as the street number to avoid a false mismatch and hence a duplicate being falsely created.

Continuing with FIG. 4, at block 410, record scores are combined to produce an overall score for the database record that includes the standardized, corresponding descriptors. In one example, once all descriptors have been scored, a k-means machine-learning approach can be used to combine record scores for the standardized, corresponding descriptors to produce an overall score for the database record in question. A training set of known matches and mismatches can be used to train a machine-learning model that is incorporated into the process using k=2 (match="Yes" or "No"). At block 412, the database record is written to database 208 in data stores 107. A database record is written or not (selectively written) based on the overall match score, corresponding to yes or no as just described, where a yes dictate the record becomes part of the compiled database of clinical investigators. Records are written to compile the database until all records have been processed. At block 414, processing device 108 determines whether there are remaining records to be processed. If so, the process repeats for each record from block 406. Otherwise, the compiled database is put into use. Adaptive feasibility is used to produce test site distributions at block 416.

Figure 5:
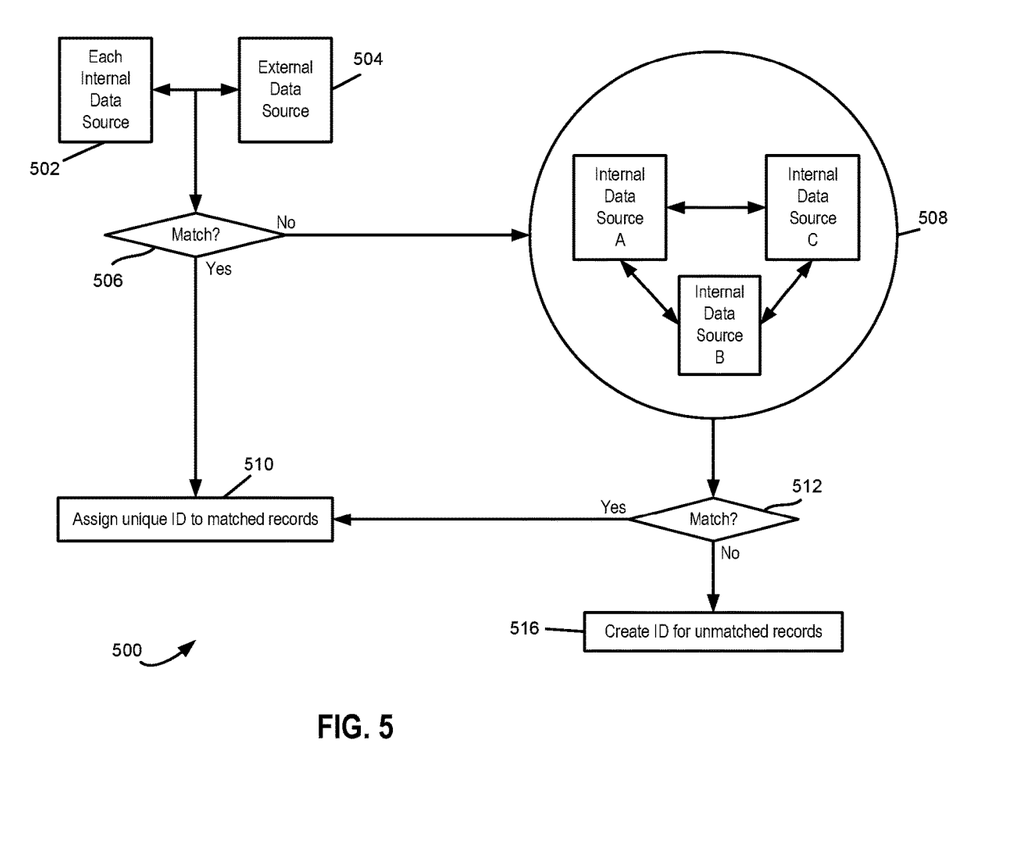
FIG. 5 is a logic diagram illustrating an example of data source matching logic flow that can be used in database reduction according to aspects of the present disclosure.

FIG. 5 is a logic diagram illustrating an example of data source matching logic flow 500 that can be used in database reduction according to aspects of the present disclosure. Database reduction begins with matching each internal data source 502 with at least one external data source 504. If there is no match at decision block 506, external data sources 508 are matched. In this example, there are three external data sources, external data source A, external data source B, and external data source C. If a match can be made at block 506 between an internal data source and an external data source, the unique ID is assigned to a matched record at block 510. Similarly, if a match can be made between internal data sources 508 at decision block 512, the unique ID is again assigned to the matched record at block 510. For records, which remain unmatched, from internal data sources 508, the system can create a unique ID at block 516. The ID created for an unmatched record can be used to locate the record for future reference.

Unless specifically stated otherwise, throughout this specification terms such as "processing," "computing," "calculating," "determining," or the like refer to actions or processes of a computing or processing device, such as one or more computers or a similar electronic computing device or devices that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computing systems accessing stored software that programs or configures the computing system from a general-purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

Aspects of the methods disclosed herein may be performed in the operation of such computing devices. The order of at some of the blocks presented in the examples above can be varied—for example, blocks can be re-ordered, combined, or broken into sub-blocks. Certain blocks or processes can be performed in parallel.

The use of "configured to" herein is meant as open and inclusive language that does not foreclose devices configured to perform additional tasks or steps. Additionally, the use of "based on" is meant to refer to actions or processes of a computing or processing device, and to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

The foregoing description of the examples, including illustrated examples, of the subject matter has been presented only for the purpose of illustration and description and is not intended to be exhaustive or to limit the subject matter to the precise forms disclosed. Numerous modifications, adaptations, and uses thereof will be apparent to those skilled in the art without departing from the scope of this subject matter. The illustrative examples described above are given to introduce the reader to the general subject matter discussed here and are not intended to limit the scope of the disclosed concepts.

What is claimed is:

1. A system comprising:
a data store;
a non-transitory computer-readable medium including computer program code for database record selection; and
a processing device communicatively coupled to the data store and the non-transitory computer-readable medium, wherein the processing device is configured for executing the computer program code to perform operations comprising:
identifying data sources for geographically clustered data containing corresponding descriptors for unique clinical trial investigators across different sources of information for database records to be written to the data store;
formatting the corresponding descriptors to produce standardized, corresponding descriptors;
matching each standardized, corresponding descriptor of the standardized corresponding descriptors to produce a record score for each standardized, corresponding descriptor;
producing, for each standardized corresponding descriptor, a modified score using the record score and a number of characters in at least one of the corresponding descriptors;
combining the modified scores for the standardized, corresponding descriptors to produce a binary overall score for each database record of the database records; and
selectively writing each database record to the data store based on the binary overall score to compile a deduplicated database of the unique clinical trial investigators.

2. The system of claim 1 wherein the operations further comprise applying a Damerau-Levenshtein algorithm to produce the modified score.

3. The system of claim 2 wherein the binary overall score is produced using a machine-learning model trained using known matches and mismatches.

4. The system of claim 1 wherein each database record corresponds to at least one of, a clinical trial investigator or a clinical trial site corresponding to the clinical trial investigator.

5. The system of claim 4 wherein the operations further comprise producing the geographically clustered data using spatial cluster analysis to determine a number of prospective clinical trial subjects within a specified distance of the clinical trial investigator from among a plurality of prospective clinical trial investigators.

6. The system of claim 5 wherein the operations further comprise:
  determining an adaptive feasibility for the clinical trial investigator; and
  producing a test site distribution for the plurality of prospective clinical trial investigators based at least in part on the adaptive feasibility.

7. The system of claim 6 wherein the operations further comprise updating the data store based on clinical trial information.

8. A method comprising:
  identifying, by a processing device, data sources for geographically clustered data containing corresponding descriptors for unique clinical trial investigators across different sources of information for database records to be written to a data store;
  formatting, by the processing device, the corresponding descriptors to produce standardized, corresponding descriptors;
  matching, by the processing device, each standardized, corresponding descriptor of the standardized corresponding descriptors to produce a record score for each standardized, corresponding descriptor;
  producing, by the processing device, for each standardized corresponding descriptor, a modified score using the record score and a number of characters in at least one of the corresponding descriptors;
  combining, by the processing device, the modified scores for the standardized, corresponding descriptors to produce a binary overall score for each database record of the database records; and
  selectively, by the processing device, writing each database record to the data store based on the binary overall score to compile a deduplicated database of the unique clinical trial investigators.

9. The method of claim 8 further comprising applying a Damerau-Levenshtein algorithm to produce the modified score.

10. The method of claim 9 wherein the binary overall score is produced using a machine-learning model trained using known matches and mismatches.

11. The method of claim 8 wherein each database record corresponds to at least one of, a clinical trial investigator or a clinical trial site corresponding to the clinical trial investigator.

12. The method of claim 11 further comprising producing the geographically clustered data using spatial cluster analysis to determine a number of prospective clinical trial subjects within a specified distance of the clinical trial investigator from among a plurality of prospective clinical trial investigators.

13. The method of claim 12 further comprising:
  determining an adaptive feasibility for the clinical trial investigator; and producing a test site distribution for the plurality of prospective clinical trial investigators based at least in part on the adaptive feasibility.

14. The method of claim 13 further comprising updating the data store based on clinical trial information.

15. A non-transitory computer-readable medium including computer program code executable by a processor to cause the processor to perform operations, the operations comprising:
  identifying data sources for geographically clustered data containing corresponding descriptors for unique clinical trial investigators across different sources of information for database records to be written to a data store;
  formatting the corresponding descriptors to produce standardized, corresponding descriptors;
  matching each standardized, corresponding descriptor of the standardized corresponding descriptors to produce a record score for each standardized, corresponding descriptor;
  producing, for each standardized corresponding descriptor, a modified score using the record score and a number of characters in at least one of the corresponding descriptors;
  combining the modified scores for the standardized, corresponding descriptors to produce a binary overall score for each database record of the database records; and
  selectively writing each database record to the data store based on the binary overall score to compile a deduplicated database of the unique clinical trial investigators.

16. The non-transitory computer-readable medium of claim 15 wherein the operations further comprise applying a Damerau-Levenshtein algorithm to produce the modified score.

17. The non-transitory computer-readable medium of claim 16 wherein the binary overall score is produced using a machine-learning model trained using known matches and mismatches.

18. The non-transitory computer-readable medium of claim 15 wherein each database record corresponds to at least one of, a clinical trial investigator or a clinical trial site corresponding to the clinical trial investigator, and the operations further comprise producing the geographically clustered data using spatial cluster analysis to determine a number of prospective clinical trial subjects within a specified distance of a clinical trial investigator from among a plurality of prospective clinical trial investigators.

19. The non-transitory computer-readable medium of claim 18 wherein the operations further comprise:
  determining an adaptive feasibility for the clinical trial investigator; and
  producing a test site distribution for the plurality of prospective clinical trial investigators based at least in part on the adaptive feasibility.

20. The non-transitory computer-readable medium of claim 19 wherein the operations further comprise updating the data store based on clinical trial information.

\* \* \* \* \*